(12) United States Patent
Wang et al.

(10) Patent No.: US 12,070,021 B2
(45) Date of Patent: Aug. 27, 2024

(54) CHIMERIC MOUSE COMPRISING STABLY TRANSPLANTED BAT CELLS

(71) Applicants: National University of Singapore, Singapore (SG); Agency for Science, Technology and Research, Singapore (SG)

(72) Inventors: Linfa Wang, Singapore (SG); Qingfeng Chen, Singapore (SG); Han Jia Justin Ng, Singapore (SG); Kylie Su Mei Yong, Singapore (SG)

(73) Assignees: NATIONAL UNIVERSITY OF SINGAPORE, Singapore (SG); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 923 days.

(21) Appl. No.: 16/650,814

(22) PCT Filed: Sep. 25, 2018

(86) PCT No.: PCT/SG2018/050488
§ 371 (c)(1),
(2) Date: Mar. 25, 2020

(87) PCT Pub. No.: WO2019/059851
PCT Pub. Date: Mar. 28, 2019

(65) Prior Publication Data
US 2020/0236913 A1   Jul. 30, 2020

(30) Foreign Application Priority Data
Sep. 25, 2017   (SG) .............................. 10201707891P

(51) Int. Cl.
*A01K 67/0271* (2024.01)
(52) U.S. Cl.
CPC ...... *A01K 67/0271* (2013.01); *A01K 2207/12* (2013.01); *A01K 2227/105* (2013.01); *A01K 2267/0337* (2013.01); *A01K 2267/0387* (2013.01)

(58) Field of Classification Search
None
See application file for complete search history.

(56) References Cited

PUBLICATIONS

Yong et al Scientific Report, 8, 1, 4726, 1-10 (Year: 2018).*
Cadili and Kneteman Transplantation Proceedings, 40, 3289-3293 (Year: 2008).*
Azuma et al, Nature Biotech. 903-910 (Year: 2007).*
Ito et al., Cellular & Molecular Immunology 9:208-214 (Year: 2012).*
Ito, M. et al. Blood 100, 3175-3182 (Year: 2002).*
Mashimo et al., PLoS One 5(1), e8870, 1-7, (Year: 2010).*
Mashimo et al., Cell Reports 2, 685-694 (Year: 2012).*
Beyer et al Stem Cell Development, 26(2), 102-112 (Year: 2017).*
Zhou et al Scientific Reports, 6:38597, 1-9 (Year: 2016).*
Ng Scientific Report, 21256, 1-18). (Year: 2016).*
Crameri et al PLoSONE, 4(12): e8266., 1-9 (Year: 2009).*
Kobak, L. et al., Hantavirus-Induced Pathogenesis In Mice With A Humanized Immune System, Journal Of General Virology, vol. 96, No. 6, pp. 1258-1263, 2015.
Mota, et al., Dengue Virus Tropism In Humanized Mice 1-24 Recapitulates Human Dengue Fever, PLoS One, vol. 6, No. 6, pp. e20762, 2011.
Zhou, et al., Unlocking Bat Immunology: Establishment Of Pferopus A/Ecto Bone Marrow-Derived Dendritic Cells And Macrophages. Scientific Reports, vol. 6, p. 38597: 1-10, 2016.
Ball, et al., Methods And Insights From The Characterization Of Osteoprogenitor Cells Of Bats (Mammalia: Chiroptera). Stem Cell Research, vol. 17, pp. 54-61, 2016.
Chua, et al., A Previously Unknown Reovirus Of Bat Origin Is Associated With An Acute Respiratory Disease In Humans. PNAS, vol. 104, No. 27, pp. 11424-11429, 2007.
Reeves, et al., Induction Of Autoimmunity By Pristane And Other Naturally Occurring Hydrocarbons, Trends Immunology, vol. 30, No. 9, pp. 455-464, 2009.
Yong, et al., Bat-Mouse Bone Marrow Chimera: A Novel Animal Model For Dissecting The Uniqueness Of The Bat Immune System, Scientific Reports, vol. 8, No. 1, pp. 4726, 2018.
International Search Report with Written Opinion, mailed Dec. 12, 2018, in International Application No. PCT/SG2018/050488.
Ahn et al., Unique loss of the PYHIN gene family in bats amongst mammals: implications for inflammasome sensing. Sci. Rep. 6; 21722, 2016.
Drake et al., Engineering humanized mice for improved hematopoietic reconstitution. Ce//. Mo/. Immunol. 9; 215-224, 2012.
King et al., Human peripheral blood leucocyte non-obese diabetic-severe combined immunodeficiency interleukin-2 receptor gamma chain gene mouse model of xenogeneic graft-versus-host-like disease and the role of host major histocompatibility complex, Clinical and Experimental Immunology, 157: 104-118, 2009.
Korngold et al., Lethal graft-versus-host disease after bone marrow transplantation across minor histocompatibility barriers in mice. Prevention by removing mature T cells from marrow. J. Exp. Med., 148, 1687-1698,1978.
Olival et al., Host and viral traits predict zoonotic spillover from mammals. Nature vol. 546, 646-650, 2017.
Ploemacher et al., An in vitro limiting-dilution assay of long-term repopulating hematopoietic stem cells in the mouse. Blood 74; 2755-2763, 1989.

(Continued)

*Primary Examiner* — Anoop K Singh
(74) *Attorney, Agent, or Firm* — Knobbe, Martens, Olson & Bear, LLP

(57) ABSTRACT

Generation of chimeric non-human animals hosting bat donor cells involves chimeric mice having bat cells that may be stably tolerated to provide a new platform technology in the general field of biology, and having application in the field of immunology related to virus-host interaction, cancer biology, autoimmunity, and the development of new drugs.

3 Claims, 8 Drawing Sheets
Specification includes a Sequence Listing.

(56) References Cited

PUBLICATIONS

Reddy et al., Mouse models of bone marrow transplantation. Biol. Blood Marrow Transplant. 14; 129-135, 2008.

Yong et al. Human CD34loCD133lo fetal liver cells support the expansion of human CD34hiCD133hi hematopoietic stem cells. Cell. Mol. Immunol. 13; 605-614 (2016).

Zhang et al. Comparative analysis of bat genomes provides insight into the evolution of flight and immunity. Science 339; 456-460 (2013).

* cited by examiner

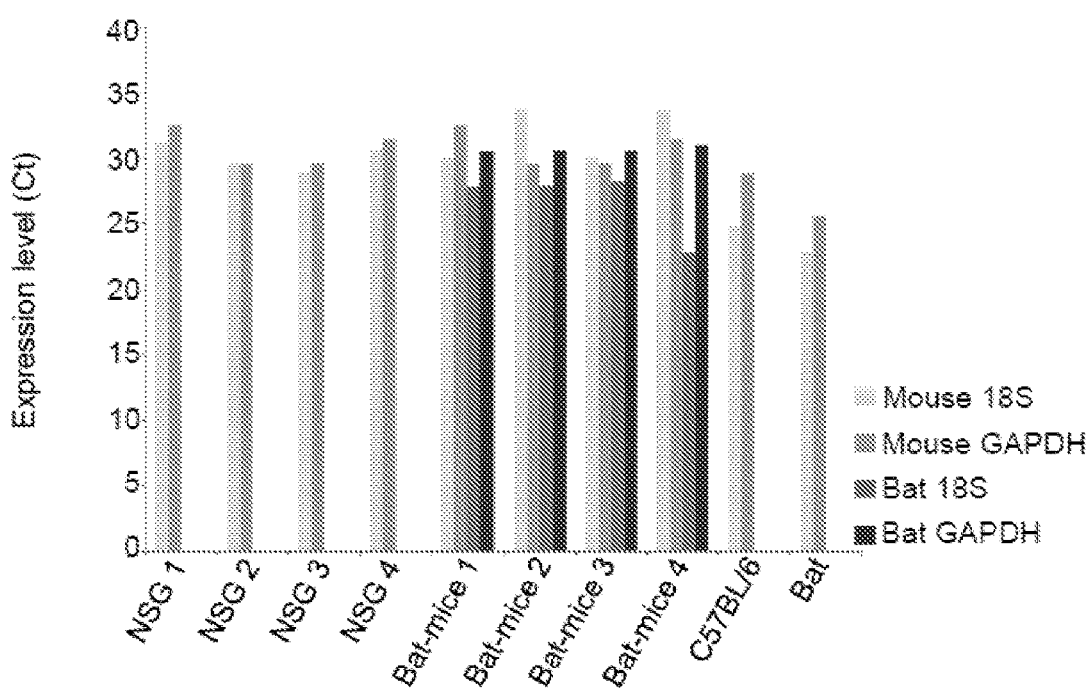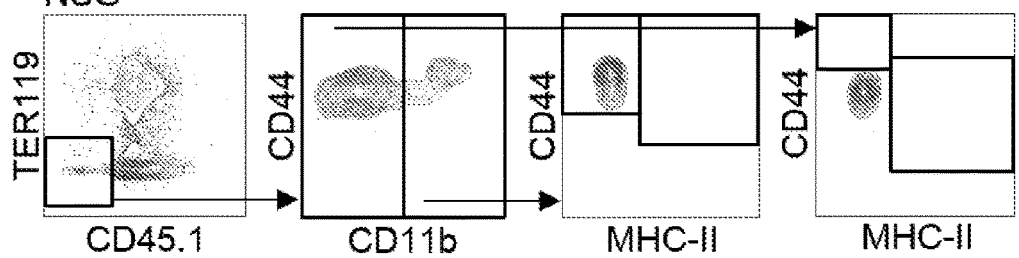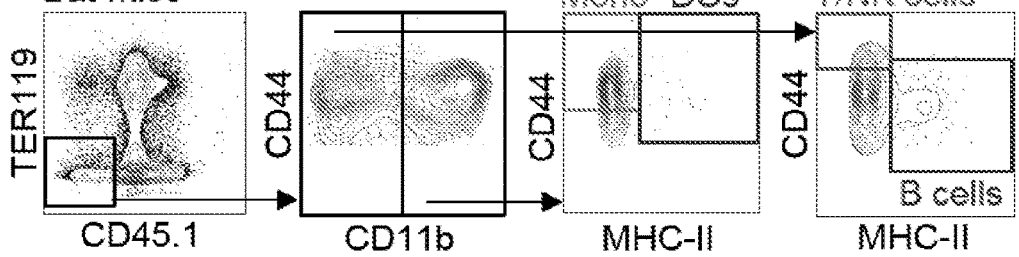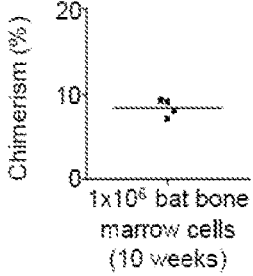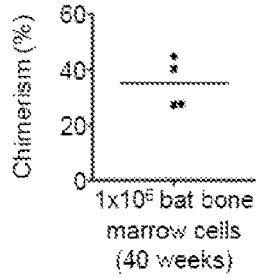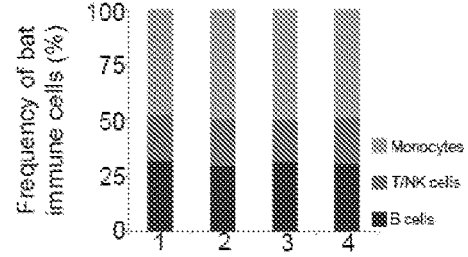
Figure 1A-F

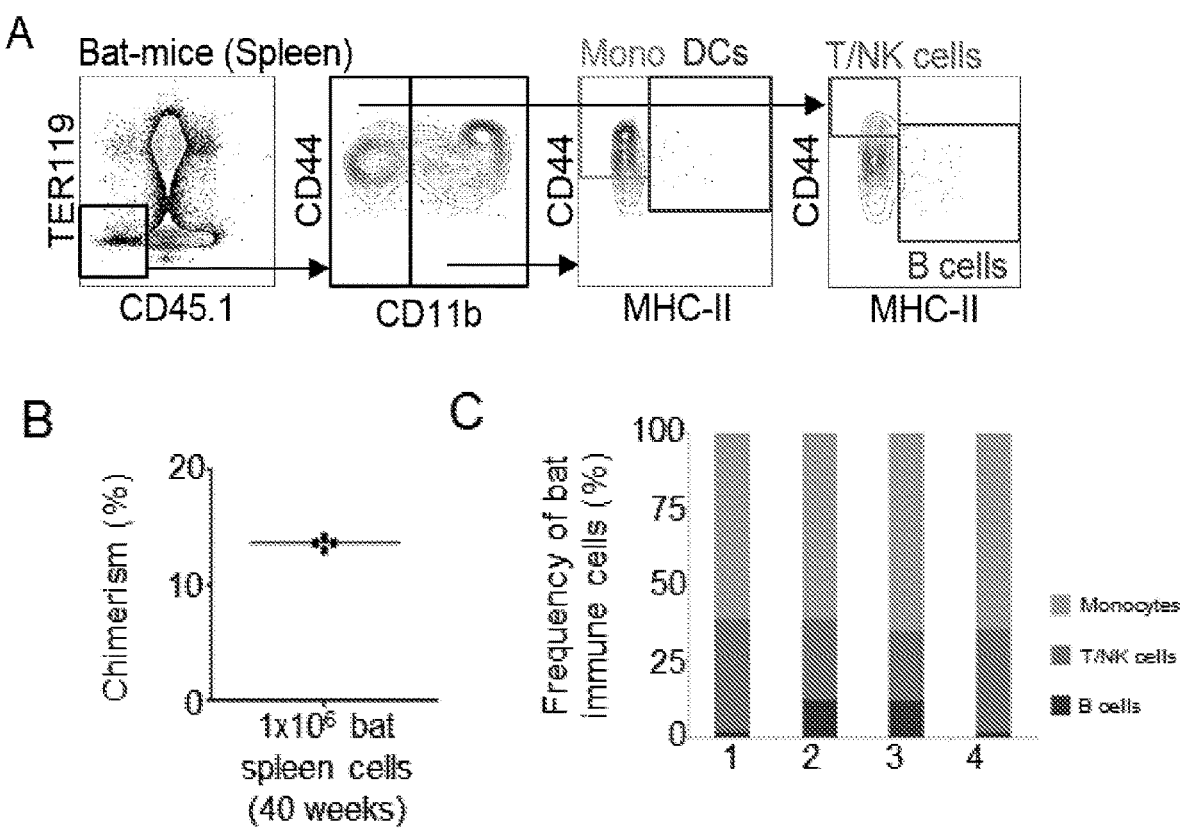
Figure 2A-C

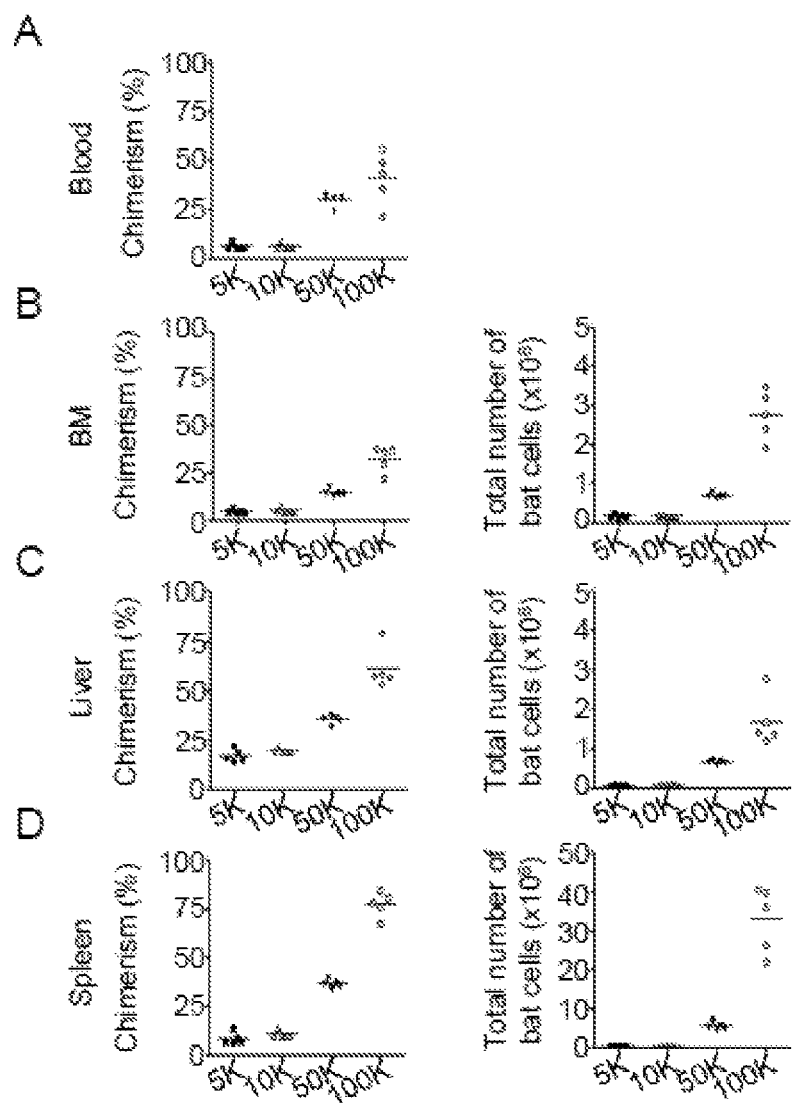
Figure 3A-D

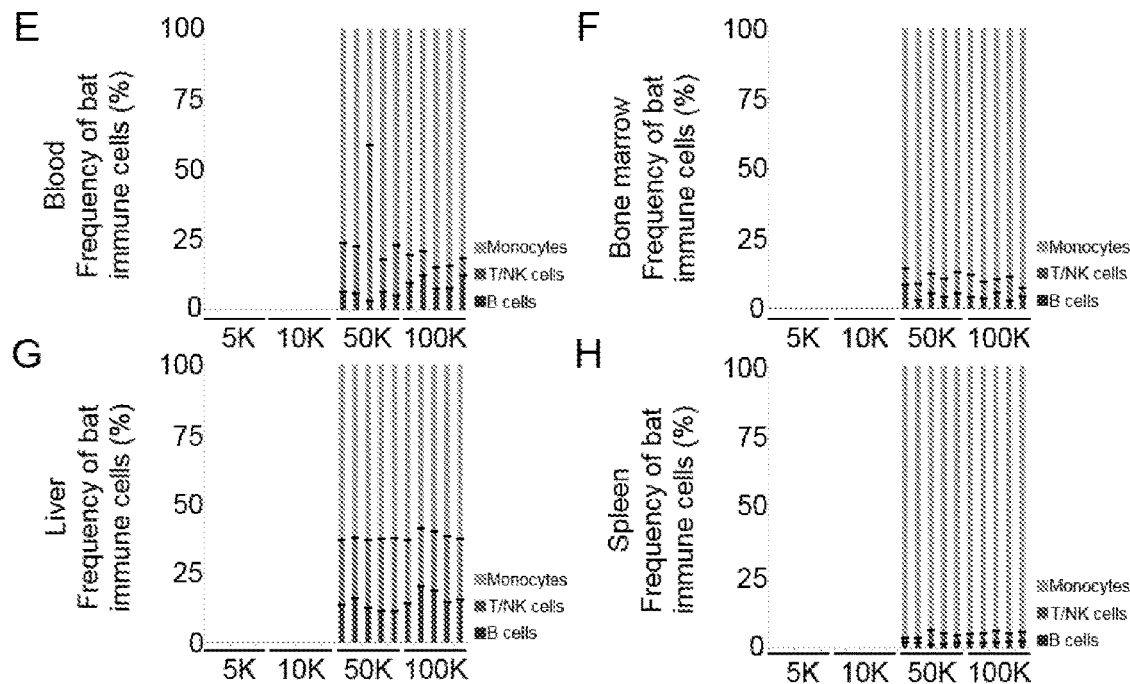
Figure 3E-H
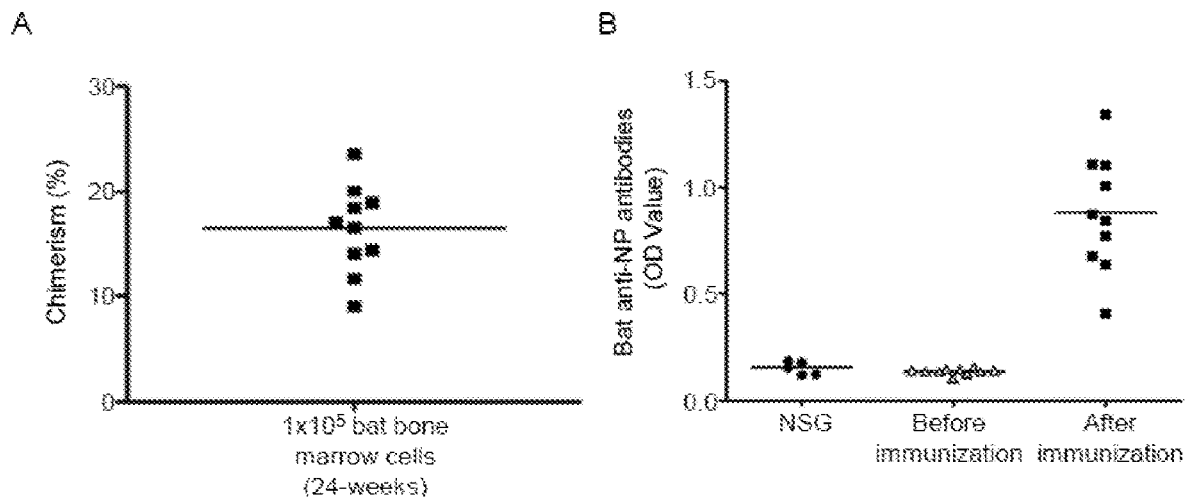
Figure 4A-B

E.s. – *Eonycteris spelaean*; M.m. – *Mus musculus*

| Genes | Sense | SEQ ID | Antisense | SEQ ID |
|---|---|---|---|---|
| E.s. 18S | TACTGCAATTAAGGGTGTAGG | 1 | CATAATGGTGATTACACGTTC | 2 |
| M.m. 18S | ACTGCCATTAAGGGCGTGG | 3 | CATGATGGTGATCACTCGC | 4 |
| E.s. GAPDH | ACCAGGGCTGCTTTTAACTC | 5 | AACTTGCCATGGGTGGAATC | 6 |
| M.m. GAPDH | CAGGGCTGCCATTTGCAG | 7 | TGAATTTGCCGTGAGTGGAG | 8 |

Figure 6

CHIMERIC MOUSE COMPRISING STABLY TRANSPLANTED BAT CELLS

FIELD OF THE INVENTION

The present invention relates to the generation of chimeric non-human animals hosting bat donor cells. More particularly, the invention relates to chimeric mice comprising bat cells which may be stably tolerated to provide a new platform technology in the general field of biology, with a main (but not the only) application in immunology, including but not limited to virus-host interaction, cancer biology, autoimmunity and the development of new drugs.

BACKGROUND OF THE INVENTION

Bats are an important nidus for an extensive spectrum of zoonotic viruses, ranging from Rabies, Henipavirus to SARS, Marburg and Ebola viruses. Being found in all continents except Antarctica, bats are not only geographically dispersed, but they also have long life spans and highly social behaviours that make them favourable hosts and vectors for disease transmission. In comparison to rodents, bats have an ability to host more zoonotic viruses per species, resulting in sympatric and cross-species infection between vertebrates, such as mammals [Olival, K. J. et al. *Nature* 546: 646-650 (2017)]. Despite possessing these characteristics, bats are remarkable creatures that are highly resistant to diseases upon infection by many of the viruses they carry. This may suggest that pathogens have a possible commensal, mutualistic relationship or specific adaptation to the bat's immune system. Comparative genomic studies have revealed an unexpected concentration of positively selected genes in the DNA damage checkpoints and immunity pathways that may be related to the origin of flight [Zhang, G. et al. *Science* 339: 456-460 (2013)]. More recently, we have reported findings from a wider comparative genomic study, indicating bats are the only mammals which have lost the entire PYHIN gene family, which codes for DNA sensors highly important for dsDNA-triggered inflammation [Ahn, M., Cui, J., Irving, A. T. & Wang, L.-F. *Sci. Rep.* 6: 21722 (2016)]. Taken together, these preliminary discoveries point to the possibility that bats have evolved an immune system, or an innate defense system that is more robust and tolerant to stress signals or stimuli (such as infection and DNA damage) as compared to other mammals, which in turn enables them to live longer and be more resilient to various pathogens. Not much is known about the bat immune system. Bat research suffers major obstacles due to the lack of bat-specific research tools (such as antibodies and specific cell lines) and, more importantly, the lack of experimental animal system due to the outbreed nature and low reproduction rates of bats. Therefore, it is of extreme importance to find an alternative system to dissect the immune system of bats, so as to discover their seemingly unique ability in controlling infections and preventing diseases.

Multiplex biological processes often require a homogenous model for both in vivo and ex vivo analysis. The study of bat biology is limited due to reasons such as: (1) wild bats of the same genetic lineage may express a wide variation in their response to the same stimulus, (2) species of interest cannot be captured from the wild freely and/or in large numbers owing to conservation and ethical reasons, (3) with innate instincts of setting up maternity colonies, it is extremely challenging to breed bats within an animal facility and their reproduction rate is much lower than rodents. To date, most bat research at the cellular and molecular level has been mainly restricted to in vitro work using non-specialised bat cell lines generated in-house. By comparison many research advances have been made using mice as a model for the study of various biological systems. Mice offer one of a kind advantage as an animal model because they are small, relatively inexpensive to maintain and, most importantly, have short generation times with an ability to produce a large number of offspring. Inbred strains are almost genetically identical, and their environment can be controlled and manipulated easily.

Over the last decade, there has been a wave of high-impact research carried out on cross-species engraftment, such as the stable reconstitution of human immune system in immunodeficient mice (humanized mouse models). The development of immunodeficient mice has provided the opportunity to utilize small animal models for the study of many in vivo human-specific immune responses. The establishment of a targeted mutation in the IL-2 receptor common gamma chain gene (IL-2R$\gamma^{-/-}$) in mice already deficient in T and B cells led to a breakthrough in the ability to engraft hematopoietic stem cells, as well as functional human lymphoid cells and tissues, effectively creating human immune systems within an immunodeficient mice. These humanized mice are becoming increasingly important as pre-clinical models for a range of studies, especially research concerning human-specific immune responses to infectious agents and drugs.

Graft versus Host Disease (GvHD) is a severe disorder that has gained significant importance because of the increasing application of cell and tissue transplants. It has been reported that the engraftment of immunologically incompatible mature cells into species such as rodent, avian, primate and human are capable of triggering GvHD responses. GvHD is the most frequent complication after transplantation and is a consequence of interactions between antigen-presenting cells of the recipients and mature T cells of the donor. In clinics, in order to reduce the risk of GvHD, mature T cells have to be depleted from donor tissues or, alternatively, only purified stem/progenitor cells can be used for transplantation. Because of this, the success of clinical transplantation is largely limited by the immunological incompatibility between donor and host cell/tissue and the high cost of tissue processing. Additionally, in order to achieve successful and stable long-term reconstitution of human immune cells in humanized mice, purified stem cells completely void of mature T cells are required to prevent the development of GvHD.

It is desirable to provide an improved animal model in which an immune system may be stably reconstituted and used to study, for example, immune tolerance to foreign pathogens and/or tissues, cancer or other biological processes.

SUMMARY OF THE INVENTION

The present invention described herein involves transplanting or engrafting bat cells into a different non-human animal, such as a mouse, to produce a chimeric animal with a reconstituted bat immune system.

Accordingly, in a first aspect, the present invention provides a chimeric non-human animal comprising xenotransplanted bat cells.

In a preferred embodiment of the invention, the bat cells are selected from a group comprising bone marrow cells, splenocytes, stem cells and lymphoid cells.

In a second aspect, the present invention provides a chimeric non-human animal as herein described, for use as a model to develop bat antibodies, to study infectious diseases, autoimmunity, aging, cancer or graft versus host disease.

In a third aspect, the present invention provides a method for producing a chimeric non-human animal comprising bat cells, comprising the steps;

a) providing bone marrow cells, splenocytes, stem cells or lymphoid cells from at least one bat; and b) introducing the bat bone marrow cells, splenocytes, stem cells or lymphoid cells into a non-human animal which has been sub-lethally irradiated, wherein the non-human animal acts as host to bat donor cells.

In a fourth aspect, the present invention provides use of a chimeric non-human animal according to any aspect of the present invention, for developing bat antibodies, to study infectious diseases, autoimmunity, aging, cancer or graft versus host disease.

In a preferred embodiment of any aspect of the present invention, the non-human animal is a mouse, more preferably an immunodeficient mouse.

BRIEF DESCRIPTION OF THE FIGURES

FIG. 1 shows measurement of reconstitution by qPCR and flow cytometry. Adult NSG mice were injected with $1\times10^6$ bat bone marrow cells. (A) Detection of bat cells in bat-mice by species-specific primers. Peripheral blood samples were taken from NSG, C57BL/6, bat-mice 40-weeks post-injection, as well as bats, and assayed by qPCR with primers specific for mouse GAPDH SEQ ID Nos: 7-8, mouse 18S RNA SEQ ID Nos: 3-4, bat GAPDH SEQ ID Nos: 5-6 and bat 18S RNA SEQ ID Nos: 1-2. Data shown are the average cycle threshold (CT) values obtained from triplicates of each sample. (B-C) Forty-week post-injection, peripheral blood from NSG (B) (n=4) and bat-mice (C) (n=4) were stained for CD45.1, Ter119, CD11b, CD44, MHC-II and analyzed by flow cytometry. Concatenated staining profiles are shown. (D-E) Chimerism levels in peripheral blood of adult NSG mice, 10-weeks (D) and 40-weeks (E) after bat BM cell injection. Each symbol represents one mouse and the horizontal line indicates the mean value. (F) Proportions of various bat immune cell populations in a representative batch of bat-mice 40 weeks post-transplantation.

FIG. 3 shows in vivo transplantation of bat bone marrow (BM) cells with limiting dilution. Bat BM cells were isolated and injected into sub-lethally irradiated NSG pups at $5\times10^3$ (5K), 133 $10^4$ (10K), $5\times10^4$ (50K) and $1\times10^5$ (100K) cells per mouse (n=5 for each group). Forty weeks later, the mice were cheek-bled and blood was prepared and analyzed by flow cytometry. (A) Shown is the plot of chimerism levels within the peripheral blood of individual mice injected with indicated number of bat bone marrow cells. Each symbol represents one mouse and the horizontal line indicates the mean value. (B-D) Chimerism levels and total bat cell count in the (B) bone marrow, (C) liver and (D) spleen of individual mouse injected with indicated number of bat bone marrow cells 40 weeks post-transplantation. Each symbol represents one mouse and the horizontal line indicates the mean value. (E-H) Percentage proportion phenotypic lymphocyte subset analysis within the (E) peripheral blood, (F) bone marrow, (G) liver and (H) spleen of bat-mice injected with bat bone marrow cells.

FIG. 4 shows determination of antigen-specific antibody response in bat-mice. Bat BM cells were isolated and injected into sub-lethally irradiated NSG pups at $1\times10^5$ cells per mouse (n=10). Twenty-four weeks post-injection, the mice were cheek-bled and blood was prepared and analyzed by flow cytometry. (A) Shown is the plot of chimerism levels within the peripheral blood of individual mice before challenge. Each symbol represents one mouse and the horizontal line indicates the mean value. (B) Bat-mice and NSG mice were challenged via intraperitoneal injection with NP-KLH, using IFA as an adjuvant. Plasma was collected from challenged bat-mice and NSG controls 2 weeks after the second booster. Optical density$_{450}$ (OD$_{450}$) levels of NP-specific antibodies were quantified by ELISA. Each symbol represents one mouse and the horizontal line indicates the mean value.

FIG. 6 shows primers for qPCR. Primer sequences SEQ ID Nos: 1-8 for bat and mouse genes.

DETAILED DESCRIPTION OF THE INVENTION

Figure 2D:
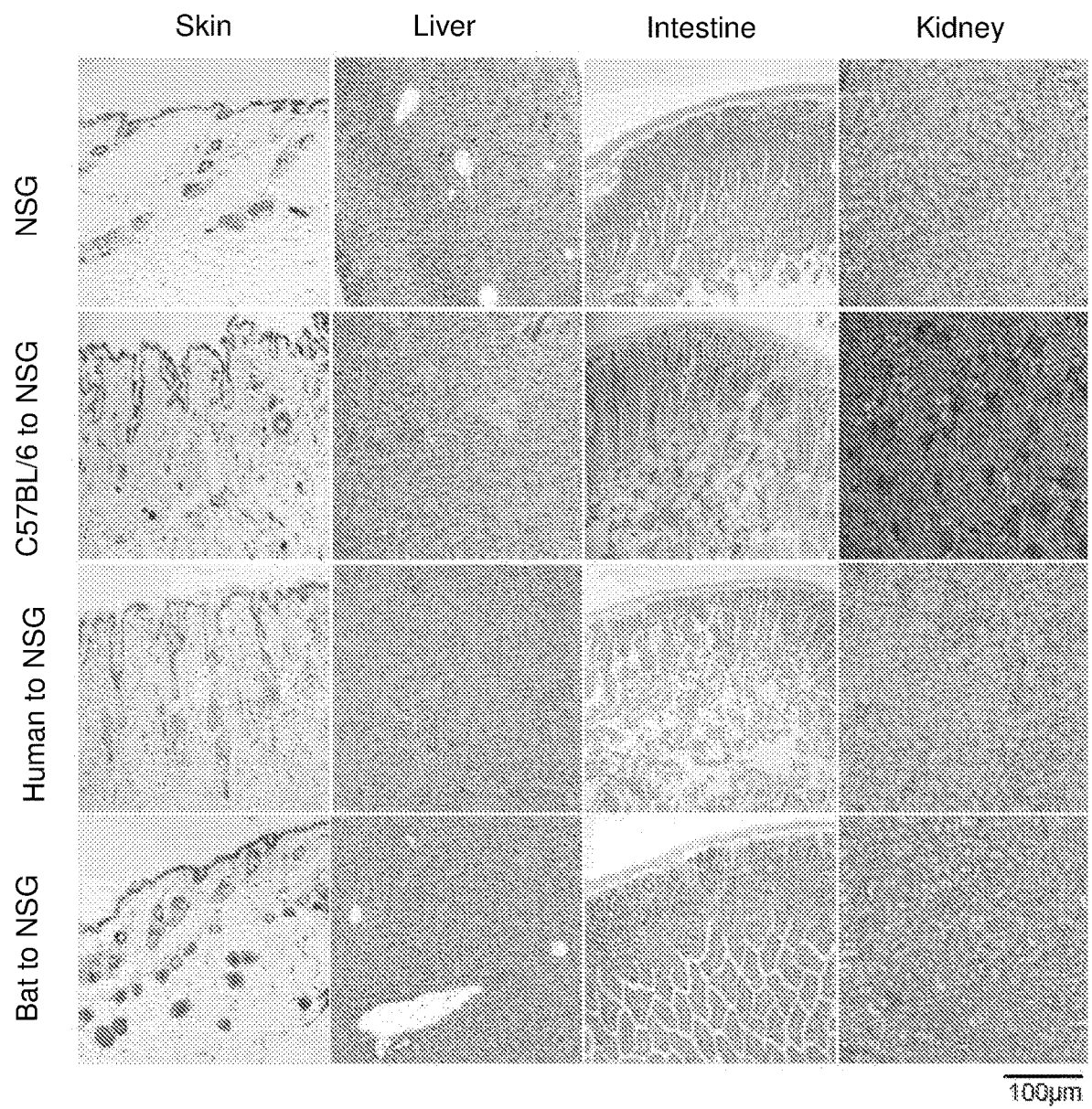
FIG. 2 shows assessment of potential GvHD in bat-mice. (A) Adult NSG mice were injected with $1\times10^6$ bat spleen cells per mouse. Peripheral blood from bat-mice (n=4) were stained for CD45.1, Ter119, CD11b, CD44 and MHC-II and analyzed by flow cytometry. Concatenated staining profiles are shown. (B) Chimerism levels in peripheral blood of adult NSG mice injected with bat spleen cells, 40 weeks post-injection. Each symbol represents one mouse and the horizontal line indicates the mean value. (C) Proportions of various bat immune cell populations in a representative batch of bat-mice. (D) and (E) Histological analysis of organs from 40-weeks-old NSG control mice (n=4), NSG mice engrafted with $1\times10^6$ C57BL/6 spleen cells 2 weeks post-injection (n=4), NSG mice engrafted with $1\times10^6$ human PBMCs 4 weeks post-injection (n=4) and NSG mice engrafted with $1\times10^6$ bat spleen cells 40 weeks post-injection (n=4). Paraffin slides made from indicated organs were processed and stained with H&E. Representative images are shown. Scale bar applies to all panels.

Bibliographic references mentioned in the present specification are for convenience listed in the form of a list of references and added at the end of the examples. The whole content of such bibliographic references is herein incorporated by reference.

Definitions

For convenience, certain terms employed in the specification, examples and appended claims are collected here.

As used herein, the term 'chimeric non-human animal' refers to a non-human animal model composed of a mixture of cells from two different species. In preferred embodiments the non-human animal is a mouse which is then engrafted with cells from a bat.

As used herein, the term 'bat donor cells' includes bone marrow cells, splenocytes, stem cells, lymphoid cells, cells from organs and/or tissues from bat origin.

As used herein, the term 'immunodeficient' refers to severe defects in innate and adaptive immunity, a lack of immune cell compartments and deficiency in cytokine signaling.

As used herein, the term 'NSG' is an abbreviation for NOD scid gamma and refers to the following mouse strain: NOD.Cg-PrkdC$^{scid}$ Il2rg$^{tm1Wjl}$/SzJ As used herein, the term 'graft versus host disease' (GVHD) is defined as a reaction that develops after an allogenic transplantation. GvHD is an immune-mediated disorder wherein the transplanted cells see the recipient's body as foreign, which results in the grafted cells attacking the new host.

As used herein, the term 'comprising' does not preclude the presence of additional steps or substances in the methods and non-human chimeric animals, respectively, of the invention, and is understood to include within its scope the terms 'consisting of' and 'consisting essentially of' features defined in the claimed invention.

The inventors have found that bat cells, such as bat bone marrow cells, splenocytes, stem cells and/or lymphoid cells can be transferred into a different species of non-human animal to generate a chimeric animal having a functional bat immune system and no apparent bat cell/tissue rejection.

Accordingly, in a first aspect, the present invention provides a chimeric non-human animal comprising xenogeneic transplanted bat cells. It would be understood that the non-human animal is not a bat and receives donor cells from a bat to become chimeric.

In a preferred embodiment of the invention, the bat cells are selected from a group comprising bone marrow cells, splenocytes, stem cells and lymphoid cells.

In another preferred embodiment of the invention, the bat cells give rise to at least one immune cell type selected from the group comprising monocytes, T cells, NK cells, B cells and dendritic cells.

In another preferred embodiment of the invention, the non-human animal is a mouse acting as host to bat donor cells.

In another preferred embodiment of the invention, the host is immunodeficient prior to receiving bat donor cells.

In another preferred embodiment of the invention, the chimeric non-human animal does not develop graft versus host disease symptoms.

In another preferred embodiment of the invention, the bat species is *Eonycteris spelaea*.

In another preferred embodiment of the invention, the bat species is *Pteropus alecto*.

In another preferred embodiment of the invention, the mouse is NOD scid gamma strain. It would be understood that other strains of immunodeficient mice would be suitable as host to the bat cells.

In a second aspect, the present invention provides a chimeric non-human animal according to any aspect of the invention for use as a model to develop bat antibodies, to study infectious diseases, autoimmunity, aging, cancer or graft versus host disease.

In a third aspect, the present invention provides a method for producing a chimeric non-human animal comprising bat cells, comprising the steps;
  a) providing bone marrow cells, splenocytes, stem cells or lymphoid cells from at least one bat; and
  b) introducing the bat bone marrow cells, splenocytes, stem cells or lymphoid cells into a non-human animal which has been sub-lethally irradiated,
wherein the non-human animal acts as host to bat donor cells.

In a preferred embodiment of the third aspect of the invention, the non-human animal is a neonate or adult.

In a preferred embodiment, the host is a mouse.

It is understood that the optimum time to create humanized mouse models with the highest level of engraftment appears to be by injecting neonatal mice within about 48 hours of birth. However the inventors have found that successful engraftment of bat cells into a mouse may also occur as late as at about 8 weeks of age.

In another preferred embodiment of the invention, the host at the time of engraftment is an 8-week-old adult mouse.

In another preferred embodiment of the invention, the host is a neonatal mouse engrafted within 48 hours of birth.

In another preferred embodiment of the invention, the host is immunodeficient prior to receiving the bat donor cells.

In another preferred embodiment of the invention, in step b) the bat donor cells are introduced by intra-hepatic or intra-venous injection.

In another preferred embodiment of the invention, the number of bat donor cells introduced is from $1 \times 10^3$ cells; such as from $5 \times 10^3$, from $1 \times 10^4$, from $5 \times 10^4$, from $1 \times 10^5$, from $5 \times 10^5$, from $1 \times 10^6$, from $5 \times 10^6$ cells, from $1 \times 10^7$ cells or any suitable number. Preferably at least $1 \times 10^5$, more preferably at least $1 \times 10^6$, bat donor cells are introduced.

Although the bat species exemplified herein is *Eonycteris spelaean*, other bat species may be suitable as cell donors for producing a chimeric non-human animal comprising bat cells.

In another preferred embodiment of the method of the invention, the bat species is selected from the group comprising *Eonycteris spelaean, Pteropus alecto* and *Myotis davidii*.

In another preferred embodiment of the method of the invention, the mouse is NOD scid gamma strain.

In another preferred embodiment, the method further comprises collecting blood samples from the chimeric non-human animal and analysing for donor and host genes and/or peripheral blood type to confirm bat chimerism.

In a fourth aspect, the present invention provides use of a chimeric non-human animal according to any aspect of the present invention, for developing bat antibodies, to study infectious diseases, autoimmunity, aging, cancer or graft versus host disease.

In a preferred embodiment of the invention there is provided a method to study zoonotic viral infection, comprising;
  i) providing NSG bat-mice and humanized mice;
  ii) infecting the mice of step i) with a zoonotic virus that causes disease in humans but does not cause clinical symptoms in host bats;
  iii) comparing the clinical symptoms and/or serological evidence of infection of the infected mice.

In a preferred embodiment, the clinical symptoms and/or serological evidence of infection are selected from the group comprising fever, weight loss, antibody production, production of inflammatory cytokines, infection of bat immune cells, the presence of virus genetic material within infected mice and death.

In a preferred embodiment, the virus is *Pteropine orthoreovirus* (PRV), also known as Melaka virus, documented to cause fever and acute respiratory diseases in human.

In a preferred embodiment, *E. spelaea* infected with Melaka virus is a negative control.

A bat-mouse model that does not display any clinical symptoms and/or serological evidence for Melaka infection, would be a good model to study other zoonotic virus infection. A screen for suitable infectious agent can be performed, to determine the suitable viruses and the optimum multiplicity of infection (MOI) ratio for each virus. How the bat immune system avoids clinical symptoms can also be investigated.

In a preferred embodiment of the invention there is provided a method to study autoimmunity, comprising;

i) providing NSG bat-mice and NSG mice;

ii) injecting a cohort of said NSG bat-mice and NSG mice intra-peritoneally with an autoimmunity-inducing agent, regardless of sex and reconstitution level;

iii) measuring the levels of human IgG, IgM, and anti-nuclear (anti-dsDNA, anti-histone, anti-RNP70, anti-SM and anti-SSA) IgGs in the plasma of the autoimmunity-inducing agent-injected bat-mice and NSG mice; and iv) comparing the levels for the injected bat-mice and NSG mice to the levels of bat IgG, IgM, and anti-nuclear (anti-dsDNA, anti-histone, anti-RNP70, anti-SM and anti-SSA) IgGs determined in the plasma of uninjected bat-mice and NSG mice.

In a preferred embodiment, the autoimmunity-inducing agent is pristane [IUPAC name 2,6,10,14-tetramethylpentadecane].

In a preferred embodiment, the NSG bat-mice and NSG mice are injected at 12-13 weeks old.

In a preferred embodiment, the levels are measured using ELISA quantification.

In another preferred embodiment of the method of the invention, the bat species is selected from the group comprising *Eonycteris spelaean, Pteropus alecto* and *Myotis davidii.*

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Green and Sambrook, Molecular Cloning: A Laboratory Manual, Cold Springs Harbor Laboratory, New York (2012).

In this study, we adopted the concept of humanized mouse models and aimed to stably reproduce bat's biological system, particularly the immune system, in mice, by transplanting bat cells (*Eonycteris spelaea*) into immunodeficient mouse strain NOD-scid IL-2R$\gamma^{-/-}$ (NSG) mice (to create what we describe as bat-mice). In this bat-mouse model, bat immune cells were successfully reconstituted in mice and unique features, such as resistance to GvHD and functional demonstration of antigen-specific bat antibody responses were observed and characterized.

Example 1

Materials and Methods

Mice

NOD-scid IL-2R$\gamma^{-/-}$ (NSG) mice were obtained from Jackson Laboratory and bred in the animal facility at A*STAR, Biological Resource Centre in Singapore. Neonatal mice within 48 hours of birth (100 rads), and 8-week old adult mice (250 rads) were sub-lethally irradiated and injected with bat cells via intra-hepatic and intravenous injection, respectively.

Bat Cell Isolation from *Eonycteris spelaea*

*Eonycteris spelaea* (common name, cave nectar bat) were captured in Singapore at dusk using mist nets and transferred to clean customized bat bags for transportation. All animal processing work was conducted in accordance with approved guidelines, methods and permits from Duke-NUS Medical School and SingHealth Experimental Medicine Centre (2015/SHS/1088). Bats were anaesthetised using isoflurane and exsanguinated via cardiac bleed. The bat was sprayed with alcohol to decontaminate the fur coat, followed by an incision from the chest to the pubis area. The spleen tissues were mashed through a 100 μm filter (Thermo scientific, USA) in DMEM medium (Thermo scientific, USA). The single-cell suspension was washed and re-suspended in media supplemented with 10% fetal bovine serum (FBS). Bone marrows were processed by making incisions on both ends of the femurs and tibias and flushing them with 5 ml of DMEM medium using 5 ml syringes (BD Biosciences, USA) and 27 gauge needles (BD Biosciences, USA). Contents flushed out of the bone marrow were mashed through a 100 μm filter in DMEM medium. The single-cell suspension was washed and re-suspended in 5 ml red blood cell lysis buffer and incubated at room temperature for 5 minutes. The cell suspension was washed and resuspended with media supplemented with 10% FBS. Cell viability was assessed using trypan blue. Prior to delivery of cells to NSG mice, cells are washed and resuspended in StemSpan™ Serum-Free Expansion Medium.

Bat Cell Isolation from *Pteropus alecto*

The bat species *Pteropus alecto,* is obtained from the Australia Bat Clinic and Wildlife Trauma Centre. Splenocytes and bone marrow cells are isolated using generally the same method as above. For these bats bone marrow cells are also harvested from the ribs and a 23 gauge needle filled with complete media is used to flush out the cells. The bone marrow cell suspension is also treated and processed for the purpose of reconstituting a bat-mouse as described for *E. spelaea.*

Processing of Mouse/Bat-Mouse Tissue

For processing of bat-mouse tissues, organs are aseptically removed from the sacrificed bat-mouse. Spleen, liver, lymph node and kidney are cut into smaller pieces and mashed through the 100 μm sieve to create single cell suspensions of the respective organs. For bone marrow cells, incisions are made on each end of the mouse tibia and femur and cells are flushed out using an 18 gauge needle and complete media. Cell suspensions are centrifuged at 1200 rpm at 4° C. for 5 minutes and supernatants are discarded. The cell pellets are resuspended in 5 ml red blood cell lysis buffer and incubated at room temperature for 5 minutes. After incubation, 7 ml of complete media is added to individual tubes. Tubes are spun at 1200 rpm at 4° C. for 5 minutes. Washing step is repeated once. Supernatants are discarded and cell pellets are resuspended in complete media or flow cytometry labelling cells (FACS) buffer.

Flow Cytometry

Conjugated antibodies for mouse CD11b (MI/70; BD Biosciences, USA), MHC-II (2G9; BD Biosciences, USA), CD45.1 (A20; Biolegend, USA), Ter119 (TER-119; Biolegend, USA) and CD44 (IML; eBioscience, USA) were used in flow cytometry assays. Cells were stained with antibodies in 100 μl PBS containing 0.2% BSA and 0.05% sodium azide for 30 minutes on ice. Flow cytometry was performed on an LSRII flow cytometer using the FACSDiva software (BD, USA); $1 \times 10^4$ events were collected per sample, and analyzed using the Flowjo software version 10 (Treestar, Ashland, USA). Percentage chimerism was calculated using the formula, [% mCD45.1$^-$Ter119$^-$/(mCD45.1 $^-$Ter119$^-$+ mCD45.1$^+$Ter119$^-$)].

Genomic DNA Extraction from Bat-Mouse

DNA extraction is performed according to the method described in E.Z.N.A® Tissue DNA Kit, product number: D3396-02.

However, instead of mincing the tissue, tissues are homogenized via FastPrep-24™ 5G Sample Preparation System (MP Biomedicals). 30 mg of tissues are added into a 2 ml Eppendorf tube with 500 μg of silicon carbide, 400 μl TL buffer and 25 μl of OB protease solution. Both TL buffer and OB protease solution are included in the E.Z.N.A® Tissue DNA Kit. Samples are homogenized by FastPrep-24™ 5G Sample Preparation System (MP Biomedicals) at 6.0 m/sec for 1 minute. After homogenization, samples are spun at 10,000×g for 5 minutes. Supernatants are collected and transferred into new Eppendorf tubes.

RNA Isolation and Quantitative Polymerase Chain Reaction (qPCR)

Blood samples were collected from NSG, C57BL/6, bat-mice and bats. RNA was prepared from these samples using RNeasy Micro kit (Qiagen, Netherlands). Reverse transcription was performed using iScript cDNA Synthesis Kit (BIO-RAD, USA) according to manufacturer's specifications. qPCR was subsequently performed in triplicates using SensiFAST™ SYBR No-ROX Kit (Bioline, USA) and assays were run on the CFX96 Touch™ Real-Time PCR Detection System (BIO-RAD, USA) under the following cycling condition: 95° C. for 5 minutes, followed by 40 cycles of 95° C. for 5 seconds and 58° C. for 30 seconds, and ending with a melt profile analysis. Sequences of bat and mouse specific primers are listed in FIG. 6 and sequence listing as SEQ ID NOs: 1-8.

Mouse Immune Challenge

Mice were challenged by injecting NP-KLH (Biosearch Technologies, USA) precipitated to IFA (Sigma-Aldrich, USA), intraperitoneally. To prepare precipitation, NP-KLH and IFA were added together and sonicated. Three injections of 100 μg of NP-KLH were used to challenge the mice. After the first challenge, mice were supplemented with booster shots which were injected on the same day for 2 consecutive weeks. Mice were bled before challenge and bled again 2 weeks following the third injection for the detection of NP-specific antibodies.

ELISA Detection of Bat Ig in Immune-Challenged Mice

Plasma was collected before and after challenging with NP-KLH by cheek bleeds or tail bleeds. Bat immunoglobulin (Ig) content specific to NP-KLH antigens was assessed by ELISA. Briefly, microtiter plates (Thermo Fisher Scientific, USA) were coated with NP31-BSA (Biosearch Technologies, USA) at 10 μg/ml. Due to the lack of anti-bat secondary antibody, pierce recombinant protein A/G horseradish peroxidase conjugate (Thermo Fisher Scientific, USA) was used as a detection reagent to Ig in plasma. As NSG mice do not have mouse T and B cells, which results in an absence of mouse Ig, the Ig detected in bat-mice sera is of bat origin. Optical density (OD) was read at 450 nm with a plate reader (Tecan, USA).

Histology

Mouse organs were collected, fixed with 10% formalin and embedded in paraffin for processing into sections. Formalin-fixed paraffin sections (4-6 μm) were dewaxed by melting for 30 minutes at 65° C., cleared in xylene twice for 5 minutes, and rehydrated in water-ethanol solutions containing decreasing percentages of ethanol. To determine tissue morphology, sections were stained with hematoxylin-eosin (Gill 2 Hematoxylin and Eosin Y alcoholic; Thermo Sandon, Cheshire, UK) following a standard procedure. Sections were imaged and analysed under an Olympus BX-61 microscope (Olympus, Japan).

Statistical Analysis

Statistical analysis was performed using GraphPad Prism 5.0 software (GraphPad Software Inc). Pairwise comparison was performed using two-tailed t test. P value less than 0.05 is considered statistically significant. All data are represented as mean.

Example 2

Transplantation of Bat Bone Marrow (BM) Cells Led to Stable Reconstitution of Bat Immune Cells in NSG Recipients Due to their immunodeficiency, NSG mice are permissive for the engraftment of foreign cells. To investigate their ability to support the engraftment of bat cells, 8 week old adult NSG mice were exposed to 2.5 Gy (250 rads) irradiation in an X ray irradiator. Post-irradiation, $1 \times 10^8$ whole bat BM cells were transferred intravenously into the treated mice. Ten weeks post-transplantation, blood samples were collected and analyzed for bat and mouse genes with species-specific primers SEQ ID Nos: 1-8 (FIG. 6) by quantitative polymerase chain reaction (qPCR). Untreated NSG mice were also kept, in parallel, as controls. Wild bat and C57BL/6 mice were used as both positive and negative controls, depending on the species-specific primers used. The results showed the presence of bat housekeeping genes (GAPDH; SEQ ID Nos: 5-6 and 18S; SEQ ID Nos: 1-2) within bat-mice, but not in control NSG mice (FIG. 1A). To further dissect the immune cell composition in blood, peripheral blood from both NSG and bat-mice were analyzed via flow cytometry. Due to the lack of bat-specific antibodies, antibodies such as anti-mouse CD11b, CD44 and major histocompatibility complex class II (MHC-II), which showed cross-reactivity with bats previously and are able to specifically bind to *E. spelaea* cells, were used. As shown in FIG. 1B and 1C, mouse-specific CD45.1 and Ter119 antibodies were used to gate out the majority of the mouse leukocytes and erythroid lineage cells. CD45.1$^-$Ter119$^-$ population was further separated into two populations by CD44 and CD11b antibodies. Within the CD44$^+$CD11b$^+$ population, monocytes and dendritic cells (DCs) were gated out by further staining with CD44 and MHC-II. From CD44$^+$CD11b$^-$ cell population, CD44 and MHC-II were used to distinguish between T/natural killer (NK) and B cells. All of the major bat immune cell populations, such as monocytes, T/NK cells, B cells and DCs were found within the peripheral blood of bat-mice (FIG. 10). Bat chimerism in bat-mouse peripheral blood was calculated by analyzing the cells that stained negative for both mouse CD45.1 and Ter119, using the formula: [% mCD45.1$^-$Ter119$^-$/(mCD45.1$^-$Ter119$^-$+mCD45.1$^+$Ter119$^-$)]. At 10 weeks post-reconstitution, the percentage of bat chimerism ranged from ~7% to 9% in the peripheral blood of four separate bat-mice in the group (FIG. 1D). Forty weeks post-transplantation, an increase in reconstitution levels, ranging from ~20% to 40%, was observed, proving long-term reconstitution is viable in the bat-mouse model (FIG. 1E). Based on the profile of bat immune cells, monocytes made up the largest proportion of cells at ~45% to 50%, followed by B cells at ~20% to ~25%, T/NK cells at ~30% to 32% and DCs at ~0.2%-1%. Bat immune cell profiles from a representative batch of bat-mice is shown in FIG. 1F. The low proportion of DCs could not be visualized due to the graphical scale used in FIG. 1F. Taken together, these results indicate that bat BM cells have a long-term repopulating capacity to survive, expand and stably establish a bat immune system in NSG recipients.

Example 3

Generation of P. alecto Bat-Mouse

Pregnant NSG mice are closely monitored towards the end of their term. 24-72-hour old pups are placed in sterile petri dishes and transferred to a sterile filter secondary container to be transported to the X ray irradiator. The pups are exposed to a total of 1 Gy (100 rads) radiation. After irradiation, pups are injected with 1-5×10$^5$ bone marrow cells or splenocytes from Pteropus alecto via the intrahepatic route. A 30 G insulin needle is used for intrahepatic injection due to the small volume injected. No anaesthesia is used on the pups as anaesthesia poses a higher death risk to the pup. After injection of bat cells, the pups are placed back into the petri dish and the sterile secondary container to be transported back to the vivarium. Pups are monitored closely for the next 72 hours. Any pup that displays any stress symptoms, is euthanized via placement on ice for 10 minutes. Reconstituted pups are weaned from their mother between 4-5 weeks old. Cheek bleeds are performed at 10 weeks post-reconstitution.

Example 4

Bat Cells Did Not Induce Graft Versus Host Disease (GvHD) in NSG Mice

Transplantation of an autologous or syngeneic graft will not trigger a rejection. However, with an allogeneic graft, wherein the donor and recipient are genetically different, the recipient will develop GvHD. The transfer of mature bat lymphoid cells was expected to cause the development of GvHD symptoms. However, it was surprising to observe that the transplantation of bat cells did not lead to any signs of GvHD in bat-mice, even 40 weeks after initial cell injection. To investigate if bat cells would generate a rejection response in NSG mice, bat splenocytes (1×10$^6$) were used for transplantation, as the majority of the cells within this organ are mature immune cells [Reddy, P., Negrin, R. & Hill, G. R. Biol. Blood Marrow Transplant. 14: 129-135 (2008)]. Forty weeks after injection, mice appeared healthy with no signs of GvHD being observed. Monocytes, T/NK cells, B cells and DCs were present in NSG mice engrafted with bat splenocytes (FIG. 2A). The reconstitution levels of bat immune cells in these mice ranged from ~12% to 15% (FIG. 2B). The overall proportions of bat monocytes, T/NK, B cells and DCs were ~60% to 65%, ~30% to 38%, ~5% to 10% and ~0-1%, respectively, in peripheral blood. Bat immune cell profiles in peripheral blood from a representative batch of bat-mice is shown in FIG. 2C. The low proportion of DCs could not be visualized due to the graphical scale used in FIG. 2C. The successful reconstitution with bat splenocytes suggested that bat mature immune cells might have the ability to expand and subsequently lead to long-term in vivo repopulation. This novel finding has never been observed before in species such as humans, mice and other mammals.

Figure 2E:
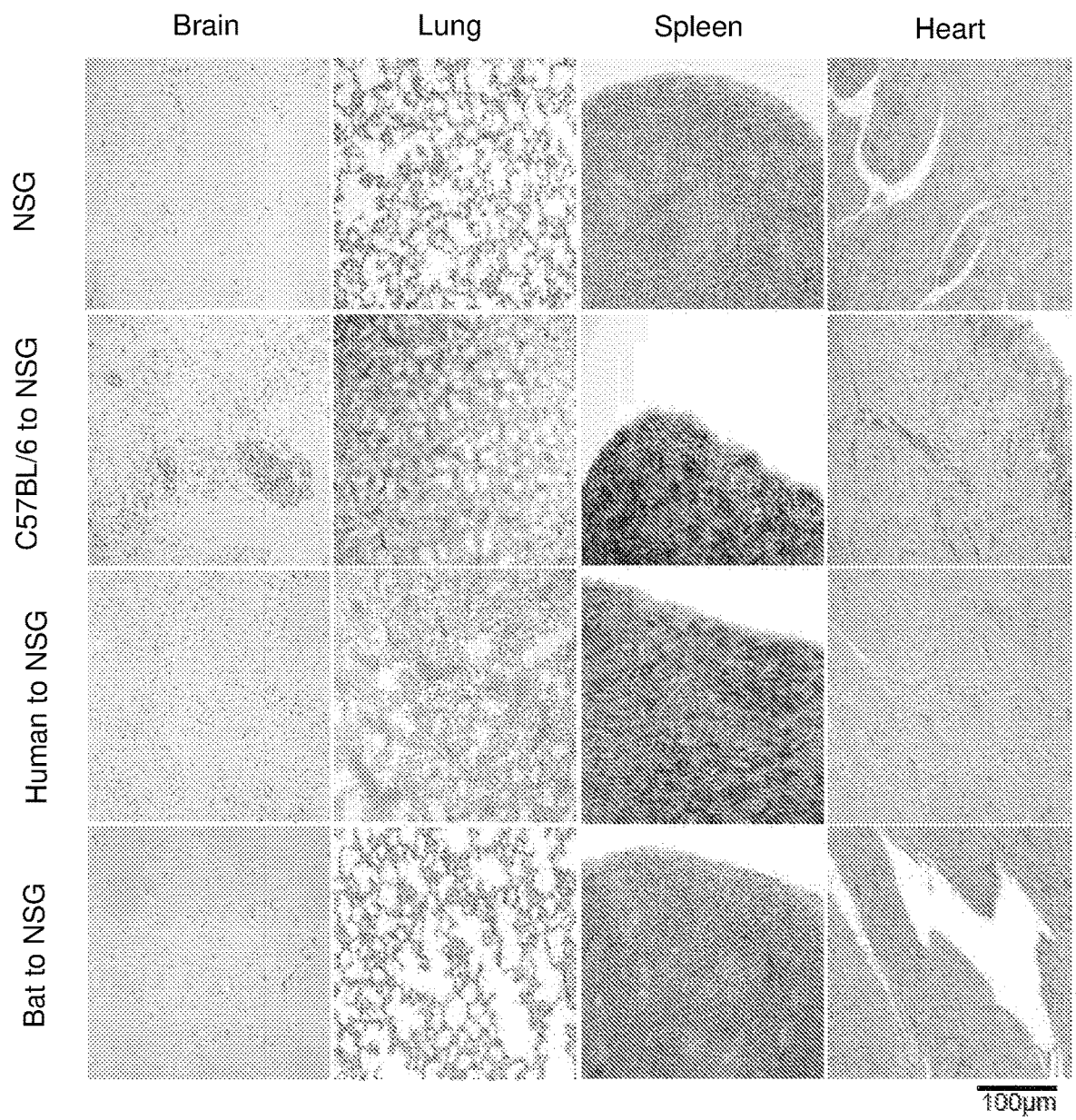

In order to uncover if bat-mice had immune-mediated tissue damage from GvHD in the absence of observable clinical signs, histological analysis was applied to assess pathological changes in different organs from bat-mice. In most acute symptoms of GvHD, the first organs affected with tissue damage are the liver, skin and intestinal tract. Transplantation of C57BL/6 splenocytes and human peripheral mononuclear cells (PBMCs) separately into NSG mice was used as a positive control as they have been known to induce GvHD in recipients with different genetic backgrounds. Two to four weeks post-transplantation, recipients of 1×10$^6$ C57BL/6 splenocytes or 1×10$^6$ human PBMCs displayed symptoms of runt disease, a condition that features small and weakened mice, characteristic of GvHD [Korngold, R. & Sprent, J. J. Exp. Med. 148: 1687-1698 (1978)]. Organs were harvested from these mice and compared to bat-mice by histological and pathological analysis. Massive cell infiltration and damage were observed in various organs from mice that received C57BL/6 splenocytes or human PBMCs, while there was no significant difference between NSG mice and bat-mice, both of which were without any evident signs of GvHD (FIG. 2D and 2E). These results confirmed that mature bat immune cells did not induce GvHD in NSG mice. In addition to the successful reconstitution of bat immune cells in mice, the present invention reveals this important and unexpected outcome: that successful engraftment of mature immune cell xenograft can be achieved with no signs of rejection. This new model will serve as a useful tool to explore deeper mechanisms on how bat immune cells develop resistance to GvHD while maintaining their functionality. Such research will also aid in the development of drugs for use in curtailing rejections in transplantations.

Example 5

Optimization of Bat Cell Engraftment in NSG Mice

Figure 5:
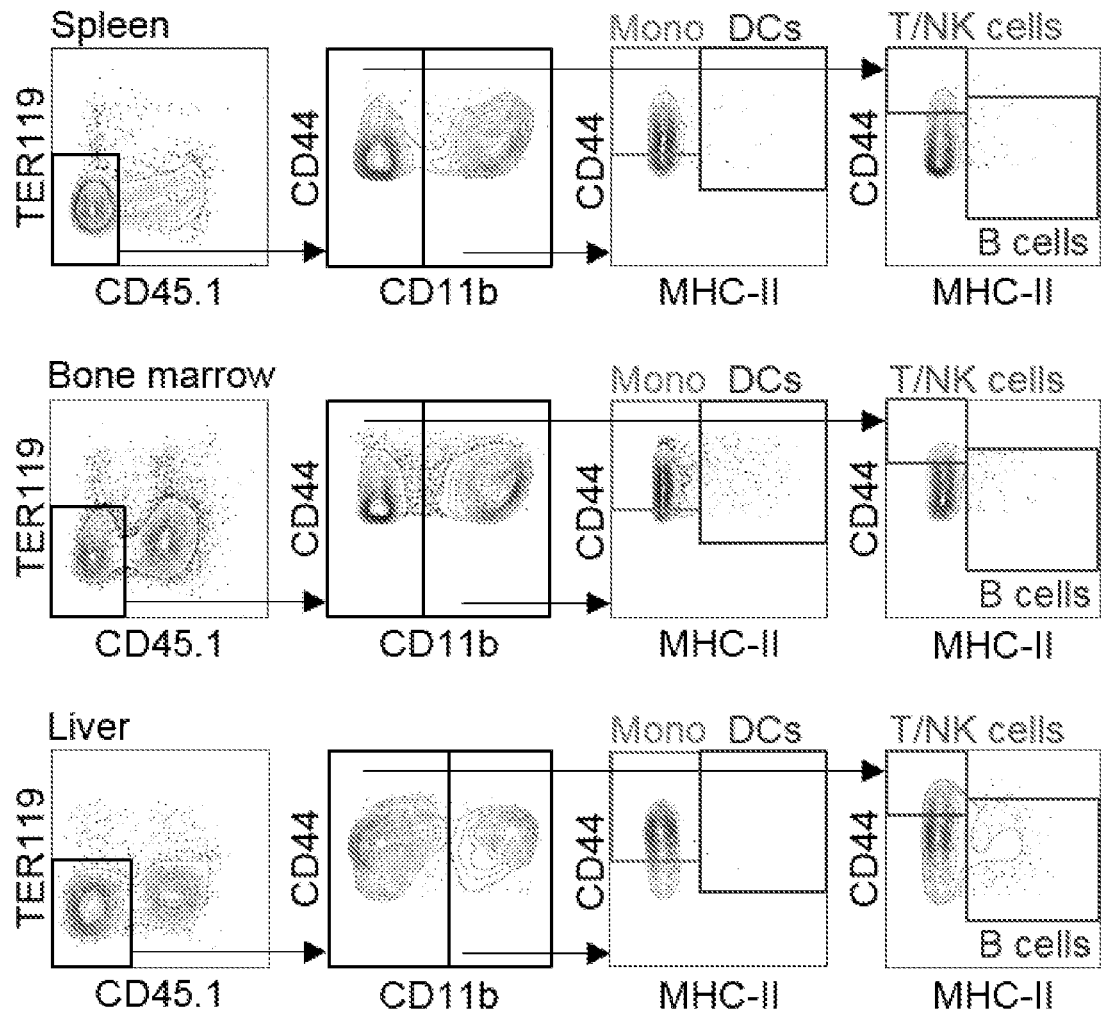
FIG. 5 shows measurement of reconstitution in organs from bat-mice by flow cytometry. Bat bone marrow (BM) cells were isolated and injected into sub-lethally irradiated NSG pups at $1\times10^5$ (100K) cells per mouse (n=5). Forty weeks later, the mice were sacrificed; organs such as spleen, BM and liver were prepared, stained for CD45.1, Ter119, CD11b, CD44, and MHC-II and analyzed by flow cytometry. Concatenated staining profiles are shown.

To optimize the production of bat-mice, further studies were conducted to improve the transplantation protocol and define the minimum number of bat BM cells needed to reconstitute NSG mice [Yong, K. S. M. et al. Cell. Mol. Immunol. 13: 605-614 (2016); Ploemacher, R. E., van der Sluijs, J. P., Voerman, J. S. & Brons, N. H. Blood 74: 2755-2763 (1989); Taswell, C. J. Immunol. 126: 1614-1619 (1981)]. As compared to adult mice, neonatal NSG are known to be better at establishing human cell repopulation in humanized mice [Drake, A. C., Chen, Q. & Chen, J. Cell. Mol. Immunol. 9: 215-224 (2012)]. Bat BM cells at varying numbers of $5\times10^3$, $1\times10^4$, $5\times10^4$ or $1\times10^5$ cells were prepared and injected into sub-lethally irradiated NSG neonates within 48 hours of birth. As shown in FIG. 3A, according to peripheral blood reconstitution levels at 40 weeks post-injection, the groups of $5\times10^3$ and $1\times10^4$ cells did not give rise to significant reconstitution, while a transfer of $5\times10^4$ or more cells resulted in engraftment. However, to achieve a robust establishment and maintenance of bat immune cells in NSG recipients, an initiating number of $1\times10^5$ bat BM cells was required to reach a reconstitution level of ~20% to 50% (FIG. 3A), which was comparable to adult NSG mice receiving $1\times10^6$ BM cells (FIG. 1E). Systemic reconstitution in various organs such as BM, liver and spleen was analyzed (FIG. 5). The bat cell chimerism levels in organs from groups of $5\times10^3$, $1\times10^4$ and $5\times10^4$ cells remained low. In mice injected with $1\times10^5$ cells, the reconstitution levels were robust, with variation in different organs: in BM, the level of bat chimerism was _~20% to 35%, with bat cell numbers ranging from ~$2\times10^6$ to $3\times10^6$ (FIG. 3B); in liver, reconstitution levels could reach ~50% to 75%, with bat cell numbers of ~$1\times10^6$ to $2\times10^6$ (FIG. 3C); spleen had the highest reconstitution levels and cell numbers, which were ~70% to 80% and ~$20\times10^6$ to $40\times10^6$, respectively (FIG. 3D). The dramatic increase in the number of bat cells within the organs, compared to the initiating number of cells injected, demonstrated that there was a massive in vivo expansion of bat cells in NSG mice (FIG. 3B to 3D). Overall proportions of immune subsets, such as monocytes, T/NK, B cells and DCs also varied between the peripheral blood, bone marrow, liver and spleen. In the peripheral blood, monocyte levels were ~40% to 70%, T/NK cells ~20% to 58%, B cells ~2% to 5% and DCs ~2% to 5% (FIG. 3E). In the bone marrow, monocytes ~80% to 95%, T/NK cells ~2% to 5%, B cells ~2% to 5% and DCs ~2% to 5% (FIG. 3F). Within the liver, the proportion of monocytes was ~60% to 62%, T/NK cells ~20% to 30%, B cells ~10% to 20% and DCs ~0% to 0.05% (FIG. 3G). The spleen was mostly dominated by monocytes, ~90% to 95%, with T/NK, B cells and DCs standing at ~2% to 5%, ~1% to 3% and ~0.5% to 2%, respectively (FIG. 3H). The low proportion of DCs in FIGS. 3E-H could not be visualized due to the graphical scale used.

Altogether, it is evident that neonatal mice, with an engraftment of a limited number of bat BM cells, were able to achieve considerable levels of chimerism with all major immune cells present, thereby enabling the reliable generation of a large cohort of bat-mice. Using the optimised protocol, we envisage that 80 to 100 bat-mice could potentially be generated from the BM of a single *E. spelaea* bat.

The unexpected discovery that bat BM cells can be successfully engrafted without rejection or GvHD is highly significant on two accounts. First, it may represent one of the strongest pieces of evidence obtained to date in support of the notion that there is immune tolerance or a dampened innate defence system in bats. Secondly, this phenomenon, which is not typically seen in mainstream immunological studies of other mammals, may open a new area for the study of immunity in unique species and create new opportunities to address human health issues. Together, this would not only allow a better understanding of bat immune responses to diseases and vaccines, but also provide a means for testing immune-modulators and exploring mechanisms in infection and neoplasia.

Example 6

The Reconstituted Bat Immune System is Functional in Bat-Mice

The demonstration of a functional bat immune system in NSG mice recipients holds a fundamental importance for the potential utility of this model. To investigate whether an antigen-specific adaptive immune response could be achieved in bat-mice, 24-week-old bat-mice that were generated by injecting $1\times10^5$ BM cells during their neonatal stage (FIG. 4A), were challenged with 4-Hydroxy-3-Nitrophenylacetyl hapten conjugated to Keyhole Limpet Hemocyanin (NP-KLH) using Incomplete Freund's Adjuvant (IFA) as an adjuvant. An ELISA-based system was customized to detect NP-specific bat antibodies using NP31-BSA as the ELISA antigen so that only NP-reacting antibodies would lead to a positive reading. Plasma samples from the 10 challenged bat-mice all showed positive reactivity with NP-antigen, whereas the pre-bleed of each bat-mouse and samples from the challenged NSG control mice were all negative (FIG. 4B). These results confirmed that bat-mice were able to generate an antigen-specific response, thereby indicating the presence of functional immune cells.

The observation of a rapid development of bat-specific antibodies post-NP-KLH challenge suggests that bat humoral immune responses involving antigen presenting cells and B cells within a mouse environment are intact and functional. Additionally, as KLH is known to be a T cell-dependent antigen which primes antigen-specific T cell responses, the responses to NP-KLH suggests that bat-mice could have developed antigen-specific T cell responses.

Example 7

Viral Infection

To investigate the feasibility of using the bat-mouse model of the present invention for viral infection studies, both *E. spelaea* and *P. alecto* bat-mice are generated as described above. In addition, humanized mice are generated to be used as a positive control. A suitable candidate virus is *Pteropine orthoreovirus* (PRV), also known as Melaka virus. Bats have been described to be the natural host for Melaka virus and do not display any clinical symptoms upon infection. By contrast, Melaka virus has been documented to cause fever and acute respiratory diseases in human. Hence, the humanized mice will display similar symptoms, such as fever and weight loss and show serological evidence of infection such as antibody production, production of inflammatory cytokines and presence of Melaka virus genetic material within infected humanized mice. Some may even die as a result of the infection. By comparison, the bat-mice do not display any clinical symptoms as the bat's immune system is immune-dampened upon virus infection. Clinical symptoms such as fever, infection of bat immune cells in bat-mice, interferon production, inflammation activation and other immune markers are measured and compared between humanized mice and bat-mice. *E. spelaea* infected with Melaka virus is the negative control for this study.

A bat-mouse model that does not display any clinical symptoms and/or serological evidence for Melaka infection, would be a good model to study other zoonotic virus infection. A screen for suitable infectious agent can be performed, to determine the suitable viruses and the optimum multiplicity of infection (MOI) ratio for each virus. How the bat immune system avoids clinical symptoms can also be investigated.

Example 8

Generation of Bat-Mice and Systemic Lupus Erythematosus (SLE) Model

To study aspects of autoimmunity, NSG pups within 3 days after birth are sub-lethally irradiated with 1 Gy γ-ray and transplanted with $1-5 \times 10^5$ bat bone marrow cells via intra-hepatic injection. Bat cell reconstitution is determined at 10-12 weeks post-transplantation by flow cytometry of the peripheral blood. Experimental mice are chosen randomly, regardless of sex and reconstitution level. Pristane [IUPAC name 2,6,10,14-tetramethylpentadecane] (Sigma Aldrich) is injected intra-peritoneally to 12-13 weeks old bat-mice and NSG mice. Levels of bat IgG, IgM, and anti-nuclear (anti-dsDNA, anti-histone, anti-RNP70, anti-SM and anti-SSA) IgGs in the plasma of control and pristane-injected bat-mice are measured using ELISA quantification kits according to manufacturer's instruction (From Bethyl laboratories, and Alpha Diagnostic Inc, respectively).

Histopathology and Immunohistochemistry

Lungs and kidneys from control and pristane-injected bat-mice and NSG mice are harvested at eight weeks post-injection, fixed with 10% formalin and embedded in paraffin for processing into 5 µm tissue sections. Rehydrated lung and kidney sections are stained with Hematoxylin & Eosin (H&E) (Thermo Scientific), and evaluated by a pathologist who is blinded to the samples' identities. Glomerular enlargement is quantified by area measurement of 50 random glomeruli from kidneys of each experimental animal. Images are captured using Brightfield slide scanner (Axio Scan Z1) and processed by Zen software (Carl Zeiss). For immunohistochemistry (IHC), kidney sections are subjected to heat-mediated antigen retrieval with sodium citrate (pH 6) buffer prior to staining with appropriate antibodies. IHC staining is performed using the SuperPicture 3rd Gen IHC Detection Kit (Life Technologies) according to manufacturer's instruction. Primary antibodies used in the study include anti-human IgG, anti-human IgM (Bethyl Laboratories), and anti-human CD45 (AbCAM). Anti-mouse, anti-rabbit and anti-goat HRP-conjugated secondary antibodies are purchased from Life Technologies.

Example 9

Stress Stimulation

While bats are known to carry multiple zoonotic viruses that are fatal to human, without displaying any clinical symptoms, less is known about bacterial infection in bats. To understand if the bat's immune system has a differential response to bacterial infection as compared to viral infection, both *P. alecto* and *E. spelaea* are injected with stimulants such as lipopolysaccharide and CpG oligodeoxynucleotides to mimic bacterial infection. Treated *P. alecto* and *E. spelaea* are euthanized 12 hours post-injection. Blood, peritoneal lavage, lung lavage, lung, liver, kidney, spleen and intestinal tissue are harvested from the bats. A portion of the tissues from each organ is frozen for proteomic works and a portion is frozen later for RNA expression studies. Lastly, the remaining tissues are processed for downstream analyses such as FACS and histology staining as described in the methods herein. The proteomic and RNA expression data from stimulated bats are compared to non-stimulated bats to determine the changes in the cytokine and chemokines profiles. The changes in the immune cell subsets upon stimulation can be identified via antibody staining and flow cytometry. In addition, these data will also be compared to data from human cells stimulated with the same stimulants. The differences between stimulated bat and human cells can help understand the "immune dampening" within the bat immune system. Lastly, the data from this study would form the baseline for future bat-mice studies to determine which cytokines are upregulated or downregulated in response to stress.

The novel bat-mouse model provided herein represents a major technical advancement and will accelerate many aspects of bat research. The bat-mouse platform provides a genetically consistent model for carrying out in vivo studies on bat immunity, as well as for other biological research.

Any listing or discussion of an apparently prior-published document in this specification should not necessarily be taken as an acknowledgement that such document is part of the state of the art or is common general knowledge.

REFERENCES

Ahn, M., Cui, J., Irving, A. T. & Wang, L.-F. Unique loss of the PYHIN gene family in bats amongst mammals: implications for inflammasome sensing. *Sci. Rep.* 6; 21722 (2016).

Drake, A. C., Chen, Q. & Chen, J. Engineering humanized mice for improved hematopoietic reconstitution. *Cell. Mol. Immunol.* 9; 215-224 (2012).

Green, M. R., Sambrook, J. Molecular cloning: a laboratory manual. *Cold Spring Harbor Laboratory Press* (2012).

Korngold, R. & Sprent, J. Lethal graft-versus-host disease after bone marrow transplantation across minor histocompatibility barriers in mice. Prevention by removing mature T cells from marrow. *J. Exp. Med.* 148; 1687-1698 (1978).

Olival, K. J., Hosseini, P. R., Zambrana-Torrelio, C., Ross, N., Bogich, T. L., & Daszak, P., Host and viral traits predict zoonotic spillover from mammals. Nature 546; 646-650 (2017).

Ploemacher, R. E., van der Sluijs, J. P., Voerman, J. S. & Brons, N. H. An in vitro limiting-dilution assay of long-term repopulating hematopoietic stem cells in the mouse. *Blood* 74; 2755-2763 (1989).

Reddy, P., Negrin, R. & Hill, G. R. Mouse models of bone marrow transplantation. *Biol. Blood Marrow Transplant.* 14; 129-135 (2008).

Taswell, C. Limiting dilution assays for the determination of immunocompetent cell frequencies. I. Data analysis. *J. Immunol.* 126; 1614-1619 (1981).

Yong, K. S. M. et al. Human CD34loCD133lo fetal liver cells support the expansion of human CD34hiCD133hi hematopoietic stem cells. *Cell. Mol. Immunol.* 13; 605-614 (2016).

Zhang, G. et al. Comparative analysis of bat genomes provides insight into the evolution of flight and immunity. *Science* 339; 456-460 (2013).

The invention claimed is:

1. A chimeric NOD-scid IL-2Rγ$^{-/-}$ mouse comprising transplanted bat cells, wherein the transplanted bat cells reconstitute bat immune system comprising bat monocytes, bat T cells, bat NK cells, and bat B cells in said chimeric mouse, wherein the chimeric mouse does not develop graft versus host disease symptoms, and wherein the transplanted bat cells are selected from the group consisting of the bone marrow cells, splenocytes and hematopoietic stem cells obtained from a bat species of *Eonycteris spelaea*, *Pteropus alecto*, or *Myotis davidii*.

2. A method for producing a chimeric mouse comprising transplanted bat cells, said method comprising:
   a) providing bat bone marrow cells, bat splenocytes, or bat hematopoietic stem cells from a bat species selected from the group consisting of *Eonycteris spelaea*, *Pteropus alecto*, and *Myotis davidii*; and
   b) introducing at least 1×10$^5$ bat bone marrow cells, splenocytes, or hematopoietic stem cells by intravenous or intrahepatic injection into a NOD-scid IL-2Rγ$^{-/-}$ immunodeficient neonatal or adult mouse which has been sub-lethally irradiated,
   thereby producing a chimeric NOD-scid IL-2Rγ$^{-/-}$ mouse comprising transplanted bat bone marrow cells, bat splenocytes or bat hematopoietic stem cells, wherein the bat cells reconstitute bat immune system comprising bat monocytes, bat T cells, bat NK cells and bat B cells in said chimeric mouse, wherein the chimeric NOD-scid IL-2Rγ$^{-/-}$ mouse does not develop graft versus host disease symptoms.

3. The method of claim 2, further comprising collecting blood samples from the chimeric NOD-scid IL-2Rγ$^{-/-}$ mouse and detecting for bat and mouse genes and/or peripheral blood type to confirm bat chimerism.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Eonycteris spelaean 18S forward PCR primer

<400> SEQUENCE: 1
tactgcaatt aagggtgtag g                                              21

<210> SEQ ID NO 2
<211> LENGTH: 21
<212> TYPE: DNA
<213> ORGANISM: Artificial Sequence
<220> FEATURE:
<223> OTHER INFORMATION: Eonycteris spelaean 18S reverse PCR primer

<400> SEQUENCE: 2
cataatggtg attacacgtt c                                              21

<210> SEQ ID NO 3
<211> LENGTH: 19
<212> TYPE: DNA
<213> ORGANISM: Artificial Sequence
<220> FEATURE:
<223> OTHER INFORMATION: Mus musculus 18S forward PCR primer

<400> SEQUENCE: 3
actgccatta agggcgtgg                                                 19

<210> SEQ ID NO 4
<211> LENGTH: 19
<212> TYPE: DNA
<213> ORGANISM: Artificial Sequence
<220> FEATURE:
<223> OTHER INFORMATION: Mus musculus 18S reverse PCR primer

<400> SEQUENCE: 4
catgatggtg atcactcgc                                                 19

<210> SEQ ID NO 5
<211> LENGTH: 20
<212> TYPE: DNA
<213> ORGANISM: Artificial Sequence
<220> FEATURE:
<223> OTHER INFORMATION: Eonycteris spelaean GAPDH forward PCR primer

<400> SEQUENCE: 5
accagggctg cttttaactc                                                20

<210> SEQ ID NO 6
<211> LENGTH: 20
<212> TYPE: DNA
<213> ORGANISM: Artificial Sequence
<220> FEATURE:
<223> OTHER INFORMATION: Eonycteris spelaean GAPDH reverse PCR primer

<400> SEQUENCE: 6
aacttgccat gggtggaatc                                                20

<210> SEQ ID NO 7
<211> LENGTH: 18
<212> TYPE: DNA
<213> ORGANISM: Artificial Sequence
```

```
<220> FEATURE:
<223> OTHER INFORMATION: Mus musculus GAPDH forward PCR primer

<400> SEQUENCE: 7
cagggctgcc atttgcag                                                 18

<210> SEQ ID NO 8
<211> LENGTH: 20
<212> TYPE: DNA
<213> ORGANISM: Artificial Sequence
<220> FEATURE:
<223> OTHER INFORMATION: Mus musculus GAPDH reverse PCR primer

<400> SEQUENCE: 8
tgaatttgcc gtgagtggag                                               20
```